(12) United States Patent
Straub et al.

(10) Patent No.: US 11,246,837 B2
(45) Date of Patent: Feb. 15, 2022

(54) ACID RESISTANT BANDING OR SEALING SOLUTION FOR ACID RESISTANT TWO PIECE HARD CAPSULES

(71) Applicant: Capsugel Belgium NV, Bornem (BE)

(72) Inventors: Hugues Straub, Colmar (FR); Jenifer Mains, Bathgate (GB)

(73) Assignee: Capsugel Belgium, NV, Bornem (BE)

( * ) Notice: Subject to any disclaimer, the term of this patent is extended or adjusted under 35 U.S.C. 154(b) by 662 days.

(21) Appl. No.: 15/772,787

(22) PCT Filed: Aug. 8, 2016

(86) PCT No.: PCT/EP2016/068834
§ 371 (c)(1),
(2) Date: May 1, 2018

(87) PCT Pub. No.: WO2017/080691
PCT Pub. Date: May 18, 2017

(65) Prior Publication Data
US 2020/0163893 A1   May 28, 2020

(30) Foreign Application Priority Data
Nov. 10, 2015   (EP) .................... 15193783

(51) Int. Cl.
*A61K 9/48* (2006.01)
*C08L 1/12* (2006.01)

(52) U.S. Cl.
CPC ............ *A61K 9/4866* (2013.01); *A61K 9/485* (2013.01); *A61K 9/4858* (2013.01); *C08L 1/12* (2013.01)

(58) Field of Classification Search
CPC ...... A61K 31/167; A61K 47/10; A61K 47/46; A61K 9/4833; A61K 9/4858; A61K 9/4866; A61K 9/4883; A61K 9/4891; A61K 9/4808; A61K 9/4816; A23V 2002/00; A23L 33/10; A23P 10/30
See application file for complete search history.

(56) References Cited

U.S. PATENT DOCUMENTS

| | | |
|---|---|---|
| 2,924,920 A | 2/1960 | Margolis |
| 3,071,513 A | 1/1963 | De Boer |
| 3,927,195 A | 12/1975 | Messora |
| 4,138,013 A | 2/1979 | Okajima |
| 4,734,149 A | 3/1988 | Brown |
| 4,756,902 A | 7/1988 | Harvey et al. |
| 4,761,932 A | 8/1988 | Harvey et al. |
| 4,816,259 A | 3/1989 | Matthews et al. |
| 4,922,682 A | 5/1990 | Tait et al. |
| 4,940,499 A | 7/1990 | Lebrun et al. |
| 5,054,208 A | 10/1991 | Gillette et al. |
| 5,283,064 A | 2/1994 | Suzuki et al. |
| 7,094,425 B2 | 8/2006 | Scott et al. |
| 7,229,639 B2 | 6/2007 | Guillard et al. |
| 8,181,425 B2 | 5/2012 | McCutcheon et al. |
| 9,452,141 B1 | 9/2016 | Chang et al. |
| 2003/0194431 A1 | 10/2003 | Miller et al. |
| 2004/0028737 A1 | 2/2004 | Deshpande et al. |
| 2004/0170688 A1 | 9/2004 | Deshmukh et al. |
| 2007/0065501 A1 | 3/2007 | He et al. |
| 2010/0212261 A1 | 8/2010 | Boldis et al. |
| 2011/0033530 A1 | 2/2011 | Skalsky et al. |
| 2012/0244219 A1 | 9/2012 | Lahav et al. |
| 2014/0360404 A1* | 12/2014 | He ................ A61K 9/4891 106/168.01 |
| 2015/0140084 A1* | 5/2015 | Takubo ............ A61K 9/4866 424/452 |
| 2017/0157058 A1 | 6/2017 | Chang et al. |

FOREIGN PATENT DOCUMENTS

| | | |
|---|---|---|
| EP | 0152517 | 8/1985 |
| EP | 0460921 | 12/1991 |
| EP | 3 178 473 | 6/2017 |
| FR | 2118883 | 8/1972 |
| GB | 759274 | 10/1956 |
| JP | S5732230 | 2/1982 |
| JP | S63117761 | 5/1988 |
| JP | H08 245423 | 9/1996 |
| JP | H0987169 | 3/1997 |
| JP | 2006016372 | 1/2006 |
| JP | 2009504630 | 2/2009 |
| JP | 2010202550 | 9/2010 |
| JP | 2015502923 | 1/2015 |
| JP | 2015522548 | 8/2015 |
| JP | 2017515825 | 6/2017 |
| JP | 2017186331 | 10/2017 |

(Continued)

OTHER PUBLICATIONS

Notice of Reasons for Refusal issued by Japan Patent Office for Japanese Application No. 2018/513348 dated Jul. 14, 2020.
"Shellac" retrieved Jan. 29, 2016 from https://en.wikipedia.org/wiki/Shellac.
Final Office action issued by U.S. Patent and Trademark Office dated Aug. 11, 2017, for U.S. Appl. No. 15/332,915.
International Search Report and Written Opinion issued for International Application No. PCT/IB2012/003133, dated Apr. 9, 2013.

(Continued)

*Primary Examiner* — Audrea B Coniglio

(74) *Attorney, Agent, or Firm* — Klarquist Sparkman, LLP

(57) ABSTRACT

The present disclosure relates to acid resistant banding solutions for two piece hard capsules endowed with acid resistant properties, and methods of making and using acid resistant banding solutions. The present disclosure also relates, in part, to methods for banding such acid resistant capsules which provides an acid resistant seal between the capsule parts and achieves acid resistance in vitro.

21 Claims, 4 Drawing Sheets

(56) References Cited

FOREIGN PATENT DOCUMENTS

| JP | 2018030863 | 3/2018 |
|----|------------|--------|
| JP | 2018083825 | 5/2018 |
| TW | 200520790 | 7/2005 |
| TW | I587880 | 10/2016 |
| WO | WO 98/18454 | 5/1998 |
| WO | WO 2005/026233 | 3/2005 |
| WO | WO 2006070578 | 7/2006 |
| WO | WO 2007/020529 | 2/2007 |
| WO | WO 2011/002972 | 1/2011 |
| WO | WO 2011/036601 | 3/2011 |

OTHER PUBLICATIONS

International Search Report and Written Opinion issued for International Application No. PCT/EP2016/068834, dated Sep. 16, 2016.
Non-final Office action issued by U.S. Patent and Trademark Office dated Apr. 6, 2017, for U.S. Appl. No. 15/332,915.
Notice of Reasons for Rejection for corresponding Japanese Patent Application No. 2014-540574, dated Jul. 12, 2016.
Notice of Reasons for Rejection issued by Japan Patent Office for Japanese Application No. 2014-540574 dated Dec. 20, 2016.

\* cited by examiner

| Solvent ratio (ethanol /demineralized water) | 80:20 | 75:25 | 60:40 | 50:50 |
|---|---|---|---|---|
| |  |  |  |  |

ACID RESISTANT BANDING OR SEALING SOLUTION FOR ACID RESISTANT TWO PIECE HARD CAPSULES

CROSS REFERENCE TO RELATED APPLICATIONS

This is a U.S. National Stage of International Application No. PCT/EP2016/068834, filed Aug. 8, 2016, which was published in English under PCT Article 21(2), which in turn claims the benefit of European Application No. 15193783.6, filed Nov. 10, 2015, which is incorporated herein in its entirety.

The present disclosure relates to acid resistant banding solutions for banding or sealing, preferably banding, acid resistant two piece hard capsules, and use of such capsules for example for oral administration of at least one of pharmaceuticals, veterinary products, foods and dietary supplements to humans or animals.

Two piece hard capsules are the oral dosage form preferred by patients, and have traditionally been made from gelatin for more than a century. Over the past twenty years, new types of hard capsules have been developed with alternative raw materials, mainly with hypromellose and pullulan. All these capsules are of immediate release or designed for releasing their content in the stomach rapidly after administration.

Efforts were made to impart a specific functionality to the hard capsules. The most successful example is the gastric resistant hard capsules which can protect the content from the acid conditions, with a delayed release or an intestinal release. Generally, such capsules are utilized in the pharmaceutical and food industries to hold pharmaceutically active materials such as medicines, vitamin preparations and other edibles both solid and liquid and protect them from the acid conditions in the stomach.

Delayed release capsules resistant to the acid conditions of the stomach were developed early on using gelatin insolubilization by treatment with formaldehyde. See, e.g., Ridgway et al., *Hard Capsule Development & Technology*, The Pharmaceutical Press, 1978, p. 11.

With the development of capsule coating technology the enteric hard capsules ("enteric coated capsules") became more popular on the pharmaceutical market. See, e.g., Ridgway et al., *Hard Capsule Development & Technology*, The Pharmaceutical Press, 1978, pp. 229 to 232.

In both above cases, the capsule itself is of immediate release, and its acid resistance is achieved by a post-manufacturing treatment of the capsule, generally after the filling of the capsule in the pharmaceutical company site.

More recently, an intrinsically acid resistant HPMC hard capsule was developed and marketed under the name of DRcaps™ capsules by CAPSUGEL®. This capsule is made with an acid resistant HPMC formula. Consequently, the capsule shell itself is acid resistant and does not need a post-fill treatment to attain acid resistance.

Further evaluation of DRcaps™ capsules has revealed that there remains a risk under some conditions for the two parts of the capsule, body and cap, to become separated; for example, under the mechanical stress of in vitro dissolution testing, notably during the in vitro disintegration test under acid conditions. Similarly, diffusion of dissolution medium into the closed capsule and/or diffusion of content from the capsule through the gap between body and cap remain a risk.

Consequently, there is a need to develop a way to effectively prevent the body-cap separation and the diffusion through the gap during the in vitro dissolution tests, and thus to improve the in vivo acid resistance performance of the final dosage form.

A number of solutions to decrease the leakage through the body-cap gap have been developed. For example, hard gelatin capsule banding with a gelatin banding solution is commonly used to prevent the content leakage during storage.

Another method to decrease leakage is to seal the cap and the body of the capsule directly to each other by means of a "sealing fluid." See, e.g., U.S. Pat. No. 3,071,513; U.S. Pat. No. 2,924,920; FR 2,118,883; EP 0152517; U.S. Pat. No. 4,756,902; FR 2 118883; EP 0152517; and U.S. Pat. No. 4,756,902. Methods of banding two piece hard capsules, as well as apparatuses for banding are disclosed, for example, in U.S. Pat. Nos. 8,181,425; 7,229,639; 7,094,425; 5,054, 208; 4,940,499; 4,922,682; 4,761,932 and 4,734,149, all of which are incorporated by reference herein.

Furthermore, the development of acid resistant capsules, and hypromellose capsules such as, for example, hydroxypropylmethylcellulose (HPMC) DRcaps™ (CAPSUGEL®) capsules, created a need to adapt the composition of the banding solution to the polymer properties in order to assure acid resistance of the banded capsule. See, e.g., WO2007/020529; WO2011/036601.

All the previously known ways of banding did not exhibit appropriate acid resistance, and therefore dissolved in acid media during in vitro testing, and also in the acid conditions of the stomach.

An attempt to overcome such drawbacks was made in WO2013/150331A1, wherein an acid resistant banding composition was achieved by formulating an acid resistant polymer in an aqueous composition comprising an alkaline compound.

However, there still exists a need to develop a safe and effective method for use in acid resistant capsules to better limit risk of leakage and deformation (or cap/body constriction) typically resulting in better acid resistance in vitro as well as better visual appearance of the banded capsules.

Definitions

As used herein, the following words, phrases, and symbols are generally intended to have the meanings as set forth below, except to the extent that the context in which they are used indicates otherwise.

The terms "optional" or "optionally" means that the subsequently described event, component, or circumstance may or may not occur, and that the description includes instances where the event, component, or circumstance occurs, and instances in which it does not.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Unless otherwise indicated, "cellulose acetate phthalate" is also referred to as CAP, and is commonly known in the field of polymers with the following alternative nomenclature: CAS registry number 9004-38-0; chemical common synonyms, such as: acetyl phthalyl cellulose, cellulose acetate hydrogen 1,2-benzenedicarboxylate, cellulose acetate hydrogen phthalate, cellulose acetate monophthalate, cellulose acetophthalate, and cellulose acetyl phthalate; and non proprietary names, such as: cellacephate (British Pharmacopeia), cellulose acetate phthalate (Japanese Pharmacopeia), cellulosi acetas phthalas (PhEur), and cellacefate (U.S. Pharmacopeia).

Unless otherwise indicated, "cellulose acetate trimellitate" is also referred to as CAT.

Unless otherwise indicated, "hydroxypropylmethylcellulose acetate succinate" is also referred to as HPMCAS.

Unless otherwise indicated, "hydroxypropyl methylcellulose phthalate" is also referred to as HPMCP.

Unless otherwise indicated, "carboxy methyl ethyl cellulose" is also referred to as CMEC.

Unless otherwise indicated, "polyvinyl derivatives" includes but is not limited to polyvinyl acetate phthalate which is also referred to as PVAP.

Unless otherwise indicated, the term "room temperature" means about 18° C. to about 28° C., and more particularly from about 20° C. to about 24° C. (22° C. +/−2° C.).

Unless otherwise indicated, the term "acid resistant two piece hard capsules" refers to two piece hard capsules described as acid resistant, or manufactured from acid resistant formulas or obtained by appropriate treatment post the capsule manufacturing, and includes but is not limited to capsules as described in WO 2011/030952, EP22236851, and/or U.S. 2010/113620 A1.

Unless otherwise indicated, the term "free of deformation" means that the constriction of the cap is less than 10%, preferably less than 9%, more preferably less than 8%. The constriction being measured by taking the largest diameter of the cap above the band and subtracting the diameter of the capsule at the location of the band, and then dividing by said largest diameter multiplied by 100. Cap constriction levels for different formulations can be seen in FIGS. 2 and 3.

BRIEF DESCRIPTION OF THE DRAWINGS

The accompanying drawings, which are incorporated in and constitute a part of the specification, illustrate presently embodiments of the present disclosure, and together with the general description given above and the detailed description of the embodiments given below, serve to explain the principles of the present disclosure.

DETAILED DESCRIPTION

Figure 1:
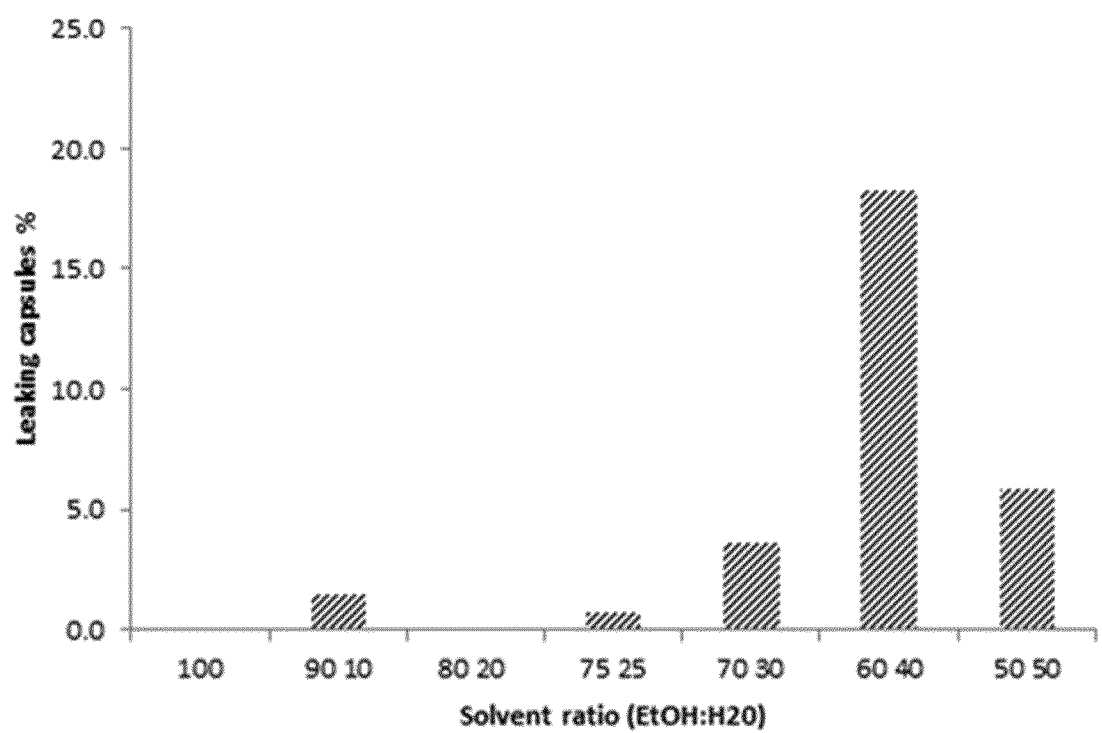
FIG. 1 illustrates the % leaking capsules following banding at different organic solvent/water ratios and subsequent vacuum challenge.

Accordingly, one aspect of the present disclosure provides acid resistant banding solutions for banding acid resistant two piece hard capsules, wherein said capsules comprise telescopically engaged capsule parts and are endowed with improved acid resistance properties compared to such capsules closed but without banding.

In an aspect, the present disclosure provides an acid-resistant banding composition comprising, preferably consisting essentially of, an acid resistant polymer, at least one neutralizing compound or material such as an alkaline (or base) compound (or material), and a mixture of organic solvent and water as solvent.

In an aspect, the present disclosure provides an acid-resistant banding composition, banding method and banded capsules, which result in improved band appearance and/or reduced leak rate.

In an aspect, the present disclosure provides a method for banding two piece capsules which provides an acid resistant seal between the capsule parts and achieves an increased acid resistance in vitro.

In a further aspect, the present disclosure relates to banding solutions for acid resistant capsules, and methods of banding acid resistant capsules with an acid resistant banding solution taking advantage of conventional banding techniques and equipment. See, e.g., F. Podczeck and B. Jones, *Pharmaceutical Capsules*, $2^{nd}$Ed., Pharmaceutical Press (2004), pp.182-183.

In an embodiment, the organic solvent comprises one or more polar solvents or short carbon-chain alcohols (C<10) or hydroxyl-group containing alcohols, preferably selected from the group consisting of isopropanol, ethanol, dimethyl sulfoxide, ethyl acetate, acetone, and mixtures thereof, preferably comprises or consists of ethanol.

Preferably, the compositions herein are free of surfactant. An advantage of this arrangement is reduced leakage. Moreover, having no surfactant may also improve drying time and disintegration performance, particularly compared to compositions comprising a water soluble surfactant.

In an embodiment, a banding composition and method for banding acid resistant hard capsules is provided comprising at least one acid resistant polymer, at least one alkaline compound, an organic solvent, and water wherein the ratio of organic solvent to water is from greater than 60:40 to 100:0, generally to less than 100:0, preferably from 65:35 to 90:10, more preferably from 70:30 to 85:15, even more preferably from 75:25 to 83:17, most preferably from 77:23 to 80:20. In particular, it has been found that for a ratio of 60:40 and less, substantial shrinkage and cap/body constriction occurs after banding the capsules. On the other hand, when the solvent consists of organic solvent (i.e. a ratio of 100:0) processing difficulties may be encountered in applying the band and is thus preferred to include water.

In an embodiment, the organic solvent is present in an amount of at least 30%, preferably at least 40%, more preferably at least 50%, even more preferably at least 60%, most preferably at least 70%, by weight of the composition.

In an embodiment, the at least one acid resistant polymer in the banding composition for hard capsules is selected from the group consisting of methacrylic acid copolymers (copolymers of methacrylic acid and either methyl methacrylate or ethyl acrylate such as poly(methacrylic acid-co-ethyl acrylate) 1:1); cellulose acetate phthalate (CAP); cellulose acetate trimellitate (CAT); hydroxypropyl methylcellulose acetate succinate (HPMCAS); hydroxypropyl methylcellulose phthalate (HPMCP); carboxy methyl ethyl cellulose (CMEC); polyvinyl derivatives (e.g., polyvinyl acetate phthalate), and mixtures thereof. The most preferred acid resistant polymer being hydroxypropyl methylcellulose acetate succinate (HPMCAS).

The acid resistant polymer may be comprised at a level of from 2% to 30%, preferably from 5% to 28%, preferably from 10% to 25%, preferably from 11% to 20%, even more preferably from 12% to 15%, by weight of the total banding composition.

As used herein, "alkaline material" refers to at least one basic compound or basic composition capable of neutralizing the acid groups of the acid resistant polymer, including but not limited to basic hydroxide compounds such as potassium hydroxide (KOH), sodium hydroxide (NaOH), calcium hydroxide (Ca(OH)$_2$), or other basic compounds or compositions, for example, ammonium hydroxide, cationic polymers such as EUDRAGIT® E PO; and mixtures thereof.

In an embodiment, the at least one alkaline compound of the banding composition is at least one compound selected from the group consisting of sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, any polymeric alkaline material such as cationic polymers and copolymers, for example cationic copolymer EUDRAGIT® E PO based on poly(2-dimethylaminoethyl methacrylate-co-butyl methacrylate-co-methyl methacrylate) 2:1:1 (IUPCAC poly(butyl methacrylate-co-(2-dimethylaminoethyl)methacrylate-co-methyl methacrylate 1:2:1) commercially available from Evonik and having an alkali value of 0.18g KOH/g polymer, organic quaternary ammonium cations or amines, and mixtures thereof. Preferably, selected from sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, and mixtures thereof.

In an embodiment, the at least one alkaline compound is present in a total amount of from 0 weight % to 5 weight % , preferably from greater than 0 weight % to 3 weight %, more preferably from 0.01 weight % to 2 weight %, even more preferably from 0.03 weight % to 1 weight %, even more preferably from 0.04 weight % to 0.7 weight %, more preferably from 0.05 weight % to 0.4 weight %, of KOH equivalent of the acid resistant polymer. For example, an amount of 0.7% NH$_3$ (35% active) by weight of the composition (with acid resistant polymer at a level of 14.2% by weight of composition), i.e. (0.7×0.35)/14.2=0.017% by weight of polymer, equates to 0.056% of KOH equivalent based on the weight of the acid resistant polymer , calculated from (0.017/17)×56 wherein the molar mass of NH$_3$=17 g/mol and the molar mass of KOH=56 g/mol.

In an embodiment, the acid resistant banding composition is applied to, and therefore further comprises, an acid resistant capsule, and in another embodiment, the acid resistant banding composition is applied to and therefore further comprises a dip molded or injection molded hydroxypropylmethylcellulose (HPMC) acid resistant capsule. In other embodiments, the acid resistant banding composition is applied to, and therefore comprises, an enteric capsule such as a dip molded HPMCAS or CAP capsule.

In an embodiment, the banding composition is applied over a band region typically extending over the outer surface of the capsule and at least a portion of the overlap portion between capsule cap and body of the telescopic capsule but nevertheless typically not more than 50%, preferably 45%, more preferably 40%, most preferably 30%, of the total external surface of the hard capsule (said total surface generally taken from the total external surface area of the capsule in an assembled state with the cap telescopically inserted over the body of the capsule in a fully closed position).

In an embodiment, the banding composition further comprises one or more film forming aids typically selected from the group consisting of hydroxypropyl methyl cellulose (HPMC) (e.g. HPMC types 2910, 2906, and/or 2208 as defined in USP3O-NF25), methylcellulose (MC), gelatin, pullulan, vinyl alcohols like PVA, starch derivatives such as hydroxypropyl starch, and mixtures thereof. Preferred are HPMC and/or MC. When included, the gelatinizing aids may be comprised at a total level of from 3% to 10%, preferably from 4% to 8%, most preferably from 4.5% to 6.5%, by weight of the total banding composition.

In an embodiment, the banding composition optionally further comprises at least one pharmaceutically acceptable or food acceptable plasticizer.

In an embodiment, the banding composition according to the present disclosure may further comprise at least one pharmaceutically acceptable or food acceptable coloring agent.

The present disclosure also provides a method for the preparation of an acid resistant banding solution comprising: dispersing at least one acid resistant polymer in a mixture comprising at least one organic solvent and water under mixing; and adding at least one alkaline compound progressively under gentle stirring until the at least one acid resistant polymer is dissolved.

In an embodiment, the method according to the present disclosure provides for the preparation of the banding solution carried out at room temperature. In another embodiment, the method according to the present disclosure provides for the use of the banding solution by banding hard capsules carried out at room temperature. Banding methods include automated and hand applied banding methods. See, e.g., *Capsule* Filling by D. K. Lightfoot, Tablets and Capsules Magazine, CSC Publishing (January 2007).

In an embodiment, the method for the preparation of an acid resistant banding solution further comprises adjusting the viscosity to a level appropriate for the hard capsule banding method. Non-limiting examples of appropriate viscosity for an acid resistant hard capsule banding solution and method are, for example, viscosities from about 50 cP (mPa·s) to about 10,000 cP; from about 100 cP to about 5000 cP; 200 cP to 3000 cP; and from about 300 cP to about 1500 cP at 21° C. (Brookfield, Spindle 27 and shear setting of 12 RPM). Desired viscosity is obtained by adjusting the concentration of the solution (i.e., by varying the amount of water and/or the amount of polymer).

In an embodiment, the banding composition herein may be used to seal the interface between the outer surface of the body and inner surface of the cap. In such embodiments it is preferred that the viscosity of the composition be from 1 cP to 1000 cP, preferably from 1 cP to 500 cP, more preferably from 1 cP to 100 cP, most preferably from 1 cP to 50 cP (i.e. low enough to allow capillary forces to draw the composition through the gap formed between capsule body and capsule cap).

In other embodiments, the method for the preparation of an acid resistant banding solution further comprises adding to the solution at least one pharmaceutically acceptable or food acceptable plasticizer and/or at least one pharmaceutically acceptable or food acceptable coloring agent.

Examples of pharmaceutically acceptable or food acceptable coloring agents include but are not limited to soluble dyes, including Tartrazine E102, FD&C Yellow 5D&C Yellow 10; Sunset Yellow E110, FD&C Yellow 6; D&C Red No. 22; D&C Red No. 28; D&C Red No. 33 (Acid Fushine); Allura Red E129, FD&C Red 40; Indigo carmine E132, FD&C Blue 2; Brilliant Blue FCF E133, FD&C Blue 1; Caramel, USP E150c; FD&C Green 3; FD&C red 3/Erythrosine; Azorubine; Brilliant Black; Chlorophyllin Copper Complex or sodium copper chlorophyllin; Ponceau 4R; Patent Blue V; Quinolone yellow; Curcumin, Red cabbage; and mixtures thereof. Other examples of pharmaceutically acceptable or food acceptable coloring agents include but are not limited to pigments, including Titanium Dioxide, Yellow Iron Oxide, Red Iron Oxide, Black Iron Oxide, Candurin silver fine, and mixtures thereof.

The present disclosure also provides a method of sealing an acid resistant hard capsule as described herein with an acid resistant banding composition as described herein, comprising the step of applying the composition over an extremity of a capsule cap proximal to an open end thereof followed by a dwelling step to allow the composition to enter and fill a gap between the outer surface of the body and inner surface of the cap (also referred to as cap/body interface), and optionally followed by a drying step to seal the cap to the body along the entire circumference of the cap/body interface.

The present disclosure also provides a method for banding an acid resistant hard capsule as described herein with an acid resistant banding composition comprising at least one acid resistant polymer, at least one alkaline compound, and water. The method includes determining the desired banding composition amount, measuring the banding composition required, and applying the banding composition to the acid resistant capsule.

The present disclosure also provides an effective acid resistant banding of acid resistant hard capsules even with low band thickness or weight, such as lower than 10 mg, or even lower than 5 mg. These values are calculated based on the quantity, deposit, and concentration of the banding solution and results obtained for the dry band weight for size 0 capsules, and will be proportional for smaller capsules. The band weight is adapted as a function of the capsule size.

The following non-limiting examples are offered to clarify the disclosure and are not intended to limit the scope of the present claims. The acid resistant capsules used in the banding examples are DRcaps™ capsules (HPMC) of size 0, natural transparent (N.T.) from CAPSUGEL®, but any acid resistant capsule may be used. The banding solutions and methods according to the present disclosure can be applied to any size of DRcaps™ capsules or to any size of other acid resistant two piece capsules. The banding solution of the present disclosure can be applied to any two piece hard capsules with acid resistance performance, for example but without limitation, enteric capsules fabricated from hydroxypropylmethylcellulose acetate succinate (HPMCAS) or from cellulose acetate phthlalate (CAP) may be banded using the banding solutions and methods according to the present disclosure.

EXAMPLES

Example 1

Table 1 illustrates three exemplary banding solutions with HPMCP (HP-55), CAP, or HPMCAS respectively as acid resistant polymer. The alkaline compound is an aqueous ammonia solution with a 35% $NH_3$ concentration (ammonia solution 0.88 S. G. (35% $NH_3$) from Fisher Scientific). The appropriate quantity by weight of polymer powder is first dispersed in an ethanol/demineralized-water mixture at room temperature under stirring to obtain the desired weight ratio. Then the indicated amount of ammonia solution is added to the dispersion progressively under gentle stirring until the polymer particles are totally dissolved. A colorant can be added, like 0.1% solution of Patent Blue V—C. I. Food Blue 5 E131 (based on the polymer weight), to aid in the visualization of the banding.

TABLE 1

| Chemical name | Supplier | Grade | Concentration (%, w/w) | Ethanol (%, w/w) | Water (%, w/w) | $NH_3$ (35%) (%, w/w) |
|---|---|---|---|---|---|---|
| HPMCP | Shin-Etsu | HP-55 | 14.9 | 76.0 | 8.4 | 0.7 |
| CAP | Eastman | CAP, NF | 14.2 | 63.8 | 21.3 | 0.7 |
| HPMCAS | Shin-Etsu | Aquot AS-LG | 14.2 | 68.1 | 17.0 | 0.7 |

Example 2

Banding solutions with HPMCAS (Aqoat AS-LG) as acid resistant polymer are made according to Example 1 (Formula 1-5 in table 2). A food grade colorant is further added to each formula to aid in the visualization of the banding.

TABLE 2

| | Formula 1 (% w/w) | Formula 2 (% w/w) | Formula 3 (% w/w) | Formula 4 (% w/w) | Formula 5 (% w/w) |
|---|---|---|---|---|---|
| HPMCAS | 14.2 | 14.2 | 14.5 | 14.2 | 14.1 |
| Ethanol | 85.1 | 63.8 | 60.8 | 51.1 | 42.6 |
| Water | 0.0 | 21.3 | 24.0 | 34.0 | 42.6 |
| $NH_3$ (35%) (%, w/w) | 0.7 | 0.7 | 0.7 | 0.7 | 0.7 |
| Ethanol:Water | 100:0 | 75:25 | 70:30 | 60:40 | 50:50 |

DRcaps™ capsules (manufactured by Capsugel®), size 0 are used for banding tests. Capsules are first filled with a liquid composition consisting of 97%wt Miglyol and 3%wt Aerosil. The filled capsules are then banded with banding compositions according to formulas 1-5 (table 2).

The band thickness or amount needed to provide an effective acid resistant banding is determined by the screening of the banding solution quantity applied on the capsule. The quantity of the banding solution applied on the capsules is determined by weighing the capsule before and immediately after the banding procedure and comparing the weights obtained. Banding is performed on a lab scale banding equipment from S1 Bench-Top Capsule Band-Sealer (Qualicaps) or MG2 (Model SL/M) with drying under room temperature conditions.

Banded capsules are then left to stand for about 12 hours at room temperature to cure.

After which intact capsules are placed on witness paper under a vacuum [depression of about −0.8 bar] and tested for leakage [the capsules are visually inspected for signs of content leaking onto the witness paper, leaking capsules are removed from the batch and the number of leaking capsules is recorded]. A population of about 400 banded capsules for each ethanol:water ratio is used as representative sample for the tests. FIG. 1 shows unacceptable leakage rate at ethanol: water ratios of less than 60:40, with the most preferred range being that of from 70:30 to 90:10.

Figure 3:
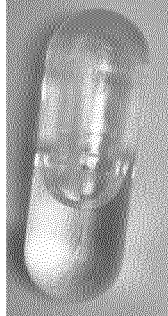
FIG. 3 illustrates photographic images showing cap/body constriction with varying organic solvent/water ratios.
Figure 3:
Figure 3:
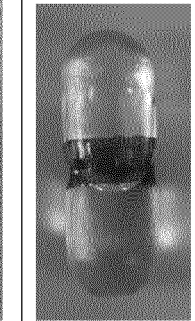
Figure 3:

The banded capsules are visually inspected for signs of constriction and/or deformation and/or shrinkage and images are taken of representative samples (see FIG. 3).

Figure 4:
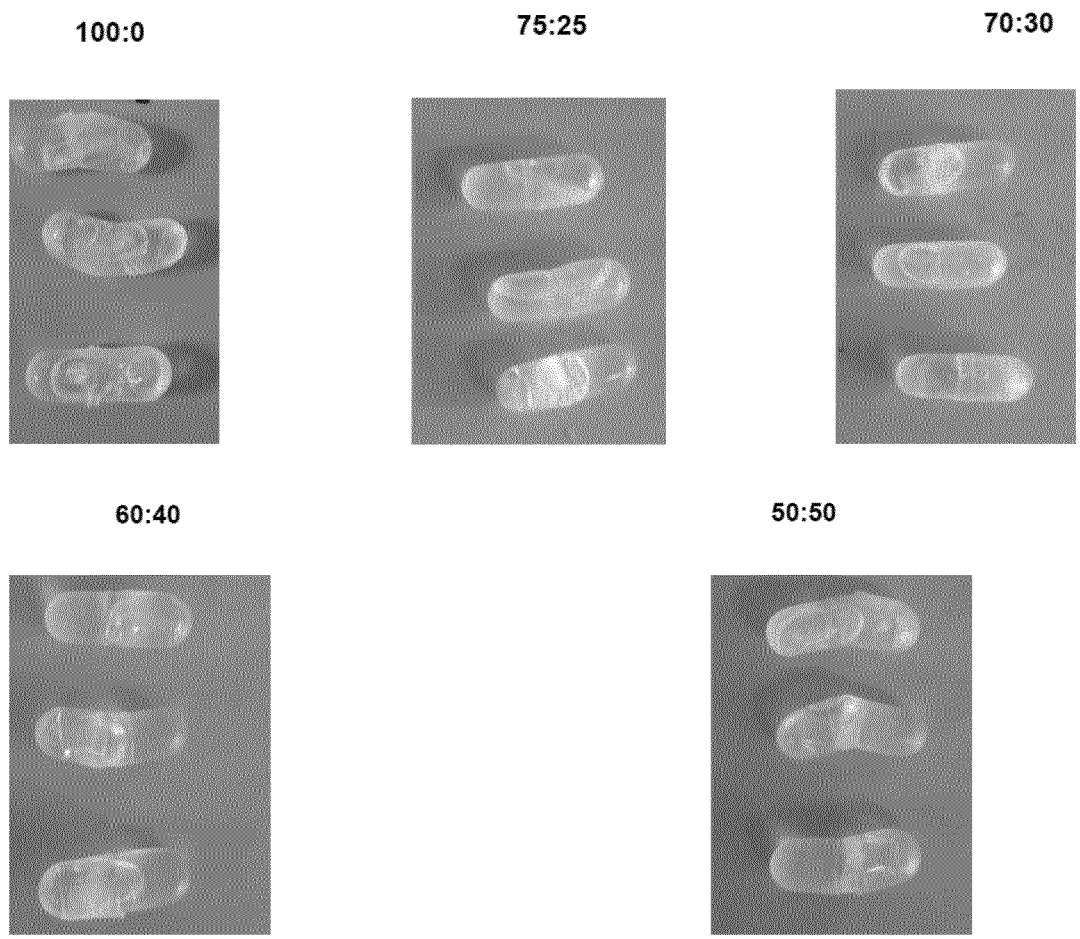
FIG. 4 illustrates photographic images showing capsule elongation following 120 minutes in 0.1 M HCl disintegration assessments with varying organic solvent/water ratios.

The banded capsules are also visually examined for deformation and/or disintegration by placing capsule samples (n=3) in 0.1 M HCl solution for two hours prior to visual inspection. Pictures are then taken of representative samples (see FIG. 4).

Example 3

Banding solutions with HPMCAS (Aqoat AS-LG) as acid resistant polymer are made according to Example 1 (table 3). A food grade colorant is further added to each formula to aid in the visualization of the banding.

TABLE 3

|  | 0:100 (wt %) | 30:70 (wt %) | 40:60 (wt %) | 50:50 (wt %) | 80:20 (wt %) | 90:10 (wt %) |
| --- | --- | --- | --- | --- | --- | --- |
| HPMCAS | 16.8 | 11.3 | 11.4 | 12.2 | 14.2 | 14.9 |
| Ethanol | — | 26.5 | 35.2 | 43.6 | 68.1 | 76 |
| Water | 81.9 | 61.7 | 52.8 | 43.6 | 17 | 8.4 |
| $NH_3$ (35%) (%, w/w) | 1.3 | 0.5 | 0.6 | 0.6 | 0.7 | 0.7 |
| Total | 100 | 100 | 100 | 100 | 100 | 100 |
| viscosity (mPa · s) | 3012 | 1005 | 1021 | 1088 | 1048 | 1167 |

Figure 2:
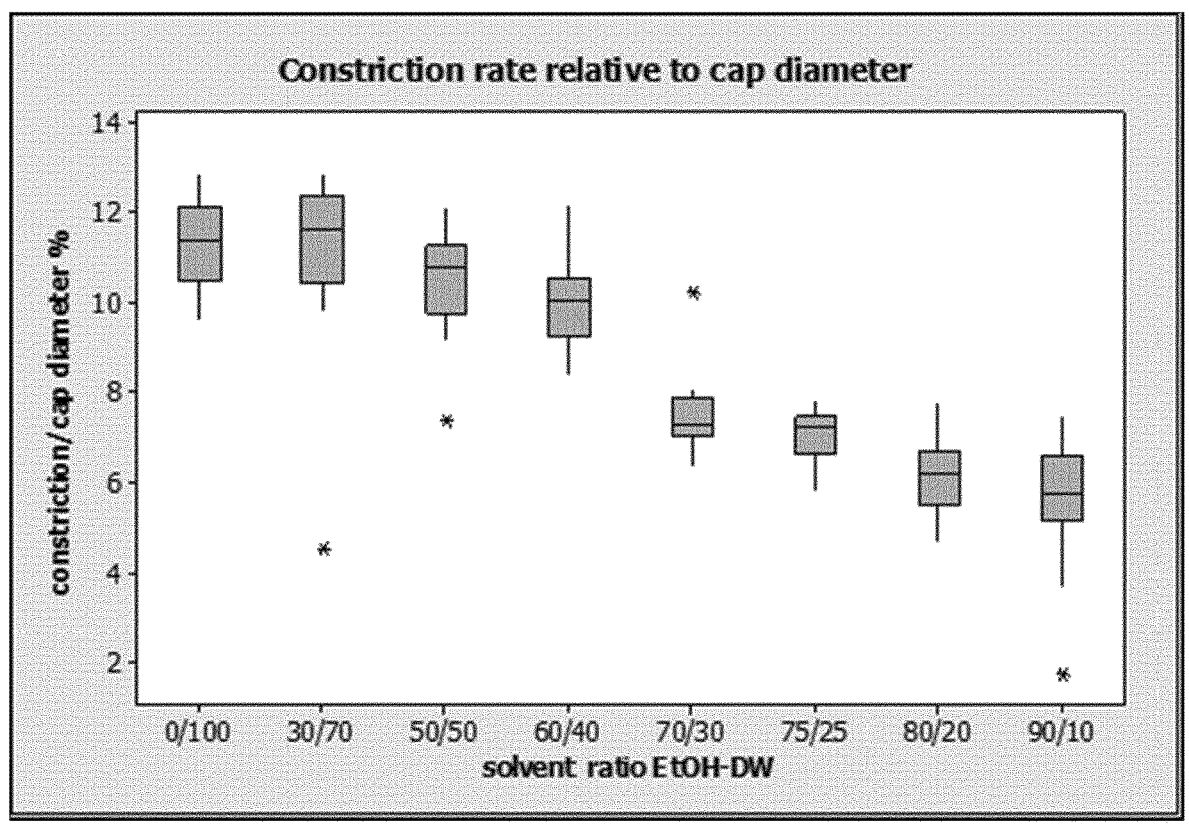
FIG. 2 illustrates banded capsule deformation with varying organic solvent/water ratios.

Band constriction is measured by microscopy and calculated by: (largest diameter of the cap prior to the band—capsule diameter at the band)/largest diameter of the cap prior to the band x 100. FIG. 2 shows a box-plot of the cap constriction measurements taken for a sample set of about n=20. Ethanol:Water ratios of greater than 70:30 show minimum constriction, with ratios of from 75:25 to, typically less than, 90:10 being the most preferred since a plateau effect is reached between ratios of 80:20 to 90:10.

In addition to DRcap™ capsules, enteric capsules such as those fabricated from HPMCAS or from CAP can also be used with the methods according to the Examples and in banding tests such as the USP disintegration method described herein.

What is claimed is:

1. A liquid acid resistant banding or sealing composition for an acid resistant two piece hard capsule, comprising HPMCAS, at least one alkaline material, ethanol, and water, wherein the weight ratio of ethanol to water is from greater than 75:25 to less than 100:0.

2. The composition according to claim 1, wherein the at least one alkaline material is sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, or any mixture thereof.

3. The composition according to claim 1, wherein the composition is configured to provide a liquid band around the two piece hard capsule.

4. The composition according to claim 1, wherein the weight ratio of ethanol to water is from 75:25 to 90:10.

5. The composition according to claim 1, wherein the ethanol is present in an amount of at least 30% by weight of the composition.

6. The composition according to claim 1, wherein the composition has a viscosity of from about 1 mPa·s to about 10,000 mPa·s at 21° C.

7. The composition according to claim 1, wherein the at least one alkaline compound is ammonia.

8. A method for preparing a liquid acid resistant banding or sealing solution, comprising:
    dispersing HPMCAS in water and ethanol under mixing, wherein the ratio of ethanol to water is from 75:25 to less than 100:0; and
    adding at least one alkaline material progressively under gentle stirring until the HPMCAS is dissolved.

9. The method according to claim 8, wherein preparing the banding solution is carried out at room temperature.

10. An acid resistant hard capsule, comprising the liquid acid resistant banding composition according to claim 1, wherein the liquid acid resistant banding composition is formed over a band region at least extending over an outer surface of the acid resistant hard capsule and over an overlapping portion of at least two telescopic pieces of wherein the band region does not cover more than 50% of the total external surface of the acid resistant hard capsule.

11. An acid resistant hard capsule, comprising the liquid acid resistant sealing composition according to claim 1, wherein the liquid acid resistant banding composition is formed over a sealing region extending only along an interface between an outer surface of a capsule body and an inner surface of a capsule cap such as to fill a gap between the body and cap with the sealing composition, wherein the sealing region extends throughout the entire circumference of the acid resistant hard capsule.

12. The capsule according to claim 10, wherein the acid resistant hard capsule is a dip molded or injection molded hydroxypropylmethylcellulose (HPMC) acid resistant hard capsule.

13. A method for banding an acid resistant hard capsule with the liquid acid resistant banding composition according to claim 1, comprising:
    determining the desired liquid acid resistant banding composition amount;
    measuring the liquid acid resistant banding composition required; and
    applying the liquid acid resistant banding composition to the acid resistant hard capsule over a band region, wherein the band region does not cover more than 50% of the total external surface of the acid resistant hard capsule.

14. The composition according to claim 1, wherein the weight ratio of ethanol to water is from 75:25 to 85:15.

15. The composition according to claim 1, wherein the ethanol is present in an amount of at least 70% by weight of the composition.

16. The composition according to claim 1, wherein the composition prevents deformation of the banded capsule such that constriction of a cap component of the banded capsule is less than 10%.

17. The method according to claim 13, wherein the band region does not cover more than 30% of the total external surface of the hard capsule.

18. The method according to claim 13, wherein the composition reduces deformation of the band region relative to a composition comprising an ethanol to water weight ratio of less than 75:25.

19. An acid resistant banding or sealing composition for an acid resistant two piece hard capsule, comprising HPMCAS, at least one alkaline material, ethanol, and water, wherein the weight ratio of ethanol to water is from greater than 60:40 to less than 100:0, and wherein the acid resistant banding or sealing composition does not comprise the acid resistant two piece hard capsule.

20. The composition according to claim 19, wherein the at least one alkaline material is sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, or any mixture thereof.

21. The composition according to claim 19, wherein the weight ratio of ethanol to water is from 75:25 to 90:10.

\* \* \* \* \*